United States Patent [19]

Arlt

[11] 4,440,947
[45] Apr. 3, 1984

[54] PREPARATION OF SUBSTITUTED ALPHA-HALOGENO-PROPIONIC ACIDS AND THEIR DERIVATIVES

[75] Inventor: Dieter Arlt, Cologne, Fed. Rep. of Germany

[73] Assignee: Bayer Aktiengesellschaft, Leverkusen, Fed. Rep. of Germany

[21] Appl. No.: 355,042

[22] Filed: Mar. 5, 1982

[30] Foreign Application Priority Data

Mar. 26, 1981 [DE] Fed. Rep. of Germany ....... 3111848

[51] Int. Cl.$^3$ ..................... C07C 61/14; C07C 51/04; C07C 53/19; C07C 17/04; C07C 19/02
[52] U.S. Cl. ................. 560/226; 260/544 Y; 260/544 D; 260/408; 562/602; 562/490; 562/496; 510/189; 510/230; 510/257; 510/261; 560/100; 560/105
[58] Field of Search ............... 260/544 Y, 408, 544 D; 560/226, 100, 105; 562/602, 490, 496; 570/189, 230, 257, 261

[56] References Cited

U.S. PATENT DOCUMENTS

| | | | |
|---|---|---|---|
| 2,410,541 | 11/1946 | Joyce | 570/189 |
| 2,515,306 | 7/1950 | Ladd et al. | 560/226 |
| 2,557,779 | 6/1951 | Critton et al. | 562/602 |
| 3,475,445 | 10/1969 | Hyatt | 570/189 |
| 3,651,019 | 3/1972 | Asscher et al. | 562/602 X |
| 3,742,047 | 6/1973 | Prill | 260/544 Y |
| 3,880,923 | 4/1975 | Scheidmeiv et al. | 260/544 Y |
| 4,053,380 | 10/1977 | Fujita et al. | 570/189 |

FOREIGN PATENT DOCUMENTS

1330693 5/1963 France .

OTHER PUBLICATIONS

Chemical Abstracts, vol. 79, 52737w, (1973).
Chemical Abstracts, vol. 54, Jan. 25, 1960, pp. 973, 974.
Chemical Abstracts, vol. 94, May 25, 1981, p. 662.

*Primary Examiner*—Natalie Trousof
*Assistant Examiner*—Vera C. Clarke

*Attorney, Agent, or Firm*—Sprung, Horn, Kramer & Woods

[57] ABSTRACT

Substituted α-halogenopropionic acids and their derivatives of the general formula

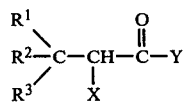
(I)

wherein $R^1$ to $R^3$, Y and X have the meanings given in the description, are prepared by a process which is characterized in that substituted vinylidene chlorides of the general formula

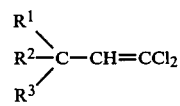
(II)

are reacted with chlorine or bromine chloride in the presence of compounds of the formula

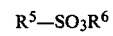
(III)

wherein $R^5$ and $R^6$ have the meaning given in the description, and the products obtained are treated, if appropriate, with water or alcohol. Certain of the substituted α-halogeno-propionic acids and the substituted vinylidene chloride of the formula

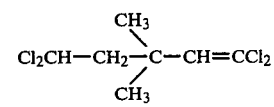

are new. The end products are useful as herbicides and intermediates for insecticides.

14 Claims, No Drawings

PREPARATION OF SUBSTITUTED ALPHA-HALOGENO-PROPIONIC ACIDS AND THEIR DERIVATIVES

The present invention relates to an unobvious process for the production of certain substituted α-halogeno-propionic acids and their derivatives, some of which are known, and to new intermediate products for their production.

It has already been disclosed that vinylidene chlorides, which are substituted by aromatic groups, can be converted into the correspondingly substituted α-halogenoacetic acid derivatives by halogenation in formic acid. However, this reaction was not known in the case of vinylidene chlorides substituted by aliphatic groups (see Chemical Abstracts 54; 1333 (1960)).

The present invention now provides a process for the production of a substituted α-halogenopropionic acid or a derivative thereof of the general formula

  (I)

in which
R$^1$ represents a hydrogen or halogen atom or an alkyl, halogen-substituted alkyl or aryl group,
R$^2$ and R$^3$ independently of each other represent a hydrogen or halogen atom or a methyl or ethyl group,
Y denotes a chlorine atom, a hydroxyl group or a group of the general formula OR$^4$,
in which
R$^4$ represents a C$_1$ to C$_8$alkyl group, and
X represents a chlorine or bromine atom,
which is characterized in that a substituted vinylidene chloride of the general formula $$R^2\underset{R^3}{\overset{R^1}{\diagdown}}C-CH=CCl_2 \quad (II)$$

wherein R$^1$, R$^2$ and R$^3$ have the meanings given above, is reacted with chlorine or bromine chloride in the presence of a compound of the general formula $$R^5-SO_3R^6 \quad (III)$$

wherein
R$^5$ represents an optionally halogen-substituted C$_1$ to C$_{18}$ alkyl group, an optionally alkyl-substituted aryl group, a C$_1$ to C$_8$ alkoxy group, a chlorine or fluorine atom or a hydroxyl group and
R$^6$ represents a hydrogen atom or a methyl or ethyl group,
and the product obtained is treated, if a compound of formula (I) in which Y represents a hydroxyl group or a group of the general formula OR$^4$ is required, with water or an alcohol R$^4$OH, respectively, wherein R$^4$ has the meaning given above.

The present invention further provides, as new compounds, substituted α-halogenopropionic acids of the general formula

  (I)

wherein
R$^1$ represents a hydrogen atom or a C$_1$ to C$_4$ alkyl group which is optionally substituted by halogen,
R$^2$ represents a hydrogen atom or a C$_1$ to C$_4$ alkyl group which is optionally substituted by halogen,
R$^3$ represents a halogen-substituted C$_1$ to C$_4$ alkyl group,
Y represents a chlorine atom, a hydroxyl group or a radical of the general formula OR$^4$, wherein
R$^4$ represents a C$_1$ to C$_8$ alkyl group, and
X represents a chlorine or bromine atom.

According to the present invention, we further provide, as a new compound, the substituted vinylidene chloride of the formula $$Cl_2CH-CH_2\underset{CH_3}{\overset{CH_3}{\diagdown}}C-CH=CCl_2 \quad (IV)$$

The present invention further provides a process for the production of the new substituted vinylidene chloride of the formula (IV), as defined above, which is characterized in that 1,3,3,3-tetrachloro-1,1-dimethyl-propane is reacted with vinyl chloride in the presence of a Lewis acid.

It is surprising that the process according to the invention for the production of compounds of formula (I) is applicable for the whole range of such compounds and proceeds with good yields in being carried out in the presence of the sulphonic acid and its esters of the formula (III), and not, as known from the state of the art, in formic acid. The process of the present invention for the production of compounds of formula (I) also has the advantage that the sulphonic acids and their esters of formula (III), which are used as the reaction medium, can readily be recovered.

If 1,1,5,5-tetrachloro-3,3-dimethyl-pent-1-ene is used as the starting compound, the process according to the invention for the production of compounds of formula (I) is illustrated by the following scheme:

The process according to the present invention is preferably used to produce compounds of the formula (I)
wherein
Y has the meaning given above,
X represent a chlorine atom,
R$^1$ represents a hydrogen atom or a C$_1$ to C$_{13}$ alkyl group which is optionally substituted by fluorine, chlorine or bromine (and preferably a hydrogen atom, a $C_1$ to $C_{13}$ alkyl group or a $C_1$ to $C_4$ alkyl group which is substituted by 1 or 2 chlorine or fluorine atoms); and $R^2$ and $R^3$ independently represent a hydrogen or halogen atom or a methyl or ethyl group (and preferably a hydrogen or chlorine atom or a methyl group).

In addition to the compounds of the formula (I) mentioned in the preparative examples, the following compounds are particularly preferred:

2,5-dichloro-3,3-dimethyl-pentanoic acid, 2-chloro-5-fluoro-3,3-dimethyl-pentanoic acid, 2,5,5-trichloro-3,3-dimethyl-pentanoic acid. 2-bromo-5,5-dichloro-3,3-dimethyl-pentanoic acid, 2-chloro-2-bromo-3-methyl-butanoic acid and 2-bromo-3,3-dimethyl-butanoic acid, as well as the acid-chlorides, and methyl, ethyl, n-propyl, i-propyl, n-butyl, i-butyl, sec.-butyl and tert. butyl esters of these acids.

The process according to the invention for the production of compounds of formula (I) is generally carried out at a temperature between $-20°$ C. and $100°$ C., preferably between $0°$ and $50°$ C.

The reaction is generally carried out under normal pressure or under slightly elevated pressure.

The halogenating agent is generally employed in an equivalent quantity relative to the vinylidene chlorides of the formula (II) employed, that is to say 1 mol of chlorine or 2 mol of bromine chloride are used per mol of the compound of the formula (II).

The following are examples of compounds of the formula (III) used in the process according to the present invention:

sulphonic acids and sulphonates, such as methanesulphonic acid, ethanesulphonic acid, chloromethanesulphonic acid, benzenesulphonic acid, o-toluenesulphonic acid, p-toluenesulphonic acid, i-dodecylbenzenesulphonic acid and methyl methanesulphonate, or sulphuric acid monoesters and diesters, such as dimethyl sulphate and diethyl sulphate, or $C_{1-8}$-alkyl and benzyl esters of chlorosulphonic acid, fluorosulphonic acid and sulphuric acid.

The reaction is particularly preferably carried out in the presence of the following compounds of the formula (III):

sulphuric acid, methanesulphonic acid, monomethyl sulphate, monoethyl sulphate and i-dodecylbenzenesulphonic acid.

The process according to the invention is preferably carried out without a solvent. However, the reaction can also be carried out in the presence of a solvent which is inert with respect to the halogenating agents used. Chloro-hydrocarbons, such as dichloromethane or dichloroethane, may be mentioned as examples of such solvents.

The process according to the invention is generally carried out in such a manner that the compounds of the formula (II), if appropriate dissolved in a solvent which is inert to halogens, are mixed with the compounds of the formula (III), and chlorine is introduced into this mixture. The end of the reaction may be determined by extracting, with hexane, a sample of the reaction mixture and investigating the extract by IR spectroscopy. The disappearance of the absorption bands at 1,600 $cm^{-1}$, which is characteristic for compounds of the formula I, indicates the end of the reaction.

To conduct away excess heat of reaction, it may be necessary to cool the mixture.

The isolation of the compounds of the formula (I) can be effected by extraction, for example with hydrocarbons such as pentane, hexane or light petrol. However, the compounds of the formula (I) can also be separated off from the reaction mixture by means of distillation.

If a compound of formula (I) which is an ester $Y=OR^4$) or an acid $(Y=OH)$ is to be obtained, it is advantageous to add at least an equivalent quantity of an appropriate alcohol or water to the reaction mixture, and to remove the ester or the acid from the reaction mixture by means of extraction or distillation.

As already mentioned, some of the compounds of the formula (I) which can be prepared by the process according to the process of the present invention are new.

Among these, the following new compounds are preferred: 2,5-dichloro-3,3-dimethyl-pentanoic acid, 2,5,5-trichloro-3,3-dimethyl-pentanoic acid, 2-bromo-5,5-dichloro-3,3-dimethyl-pentanoic acid and 2-chloro-5-fluoro-3,3-dimethyl-pentanoic acid.

The new compounds of the formula (I) can be employed as herbicides. However, some of them can also be further processed, in a process which does not yet belong to the state of the art, to give the known caronaldehyde acid. This process can be represented by the following scheme:

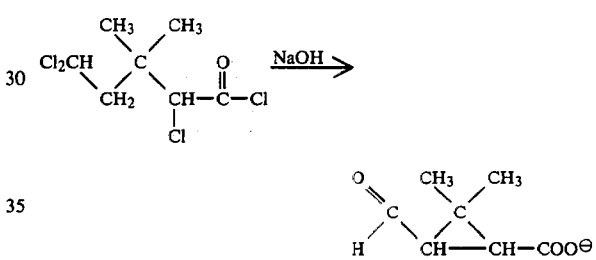

For this purpose, compounds of the formula (I) are treated, in water-containing solvents with bases such as alkali metal hydroxide or alkaline earth metal hydroxide, and the resulting salts of carbonaldehyde acid are acidified and the acid is isolated in the customary manner.

Some of the new compounds can also be further processed, in a process which does not yet belong to the state of the art, to give the known permethrinic acid. This process can be represented by the following scheme:

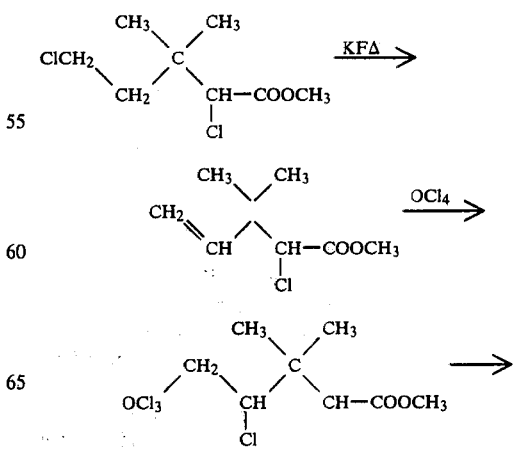

-continued

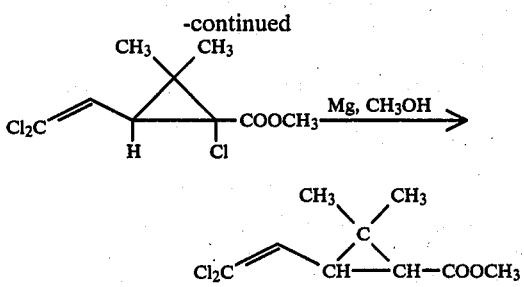

In this process, the individual process stages are carried out analogously to known processes.

The invention also relates to the process for the preparation of the novel substituted vinylidene chloride of the formula

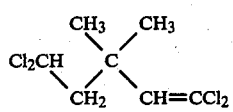  (IV)

This compound is prepared by the previously mentioned further process according to the present invention. This process can be represented by the following equation:

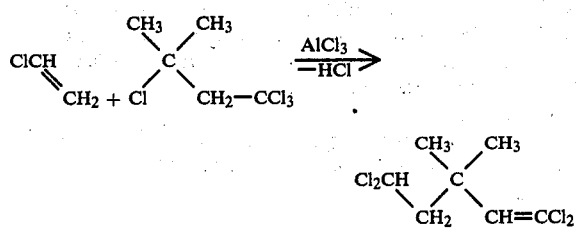

The reaction is generally carried out at a temperature between −20° C. and +30° C., preferably a temperature between −5° and +30° C. It is preferably carried out without a solvent. However, inert organic solvents, such as halogeno-hydrocarbons (for example methylene chloride) can also be used.

The tetrachlorodimethylpropane and vinyl chloride are generally employed in an equimolar ratio. The reaction is carried out in the presence of a Lewis acid. $AlCl_3$, $AlBr_3$, $BeCl_2$, $ZnCl_2$, $BF_3$, $TiCl_4$, $SnCl_4$, $SbCl_5$ and $FeCl_3$ are examples of suitable Lewis acids. The following are preferably used: $AlCl_3$, $FeCl_3$, $ZnCl_2$ and $TiCl_4$.

Surprisingly, the reaction proceeds with a good selectivity, although secondary reactions of the resulting new vinylidene chlorides of the formula (II), and elimination reactions of the tetrachlorodimethylpropane as well as the vinylidene chloride were to have been expected.

Some of the remaining compounds of the formula (II) which are used as starting materials for the process according to the invention for the production of a compound of formula (I), are known or are obtained analogously to known processes (see, for example, J. Am. Chem. Soc. 74, 2885 (1952) or Application Ser. No. 281,614, filed July 9, 1981, now pending, which does not yet belong to the state of the art).

The following examples merely serve to illustrate the processes of the present invention.

EXAMPLE 1

182 g of 1,1,5,5-tetrachloro-3,3-dimethyl-pent-1-ene were dissolved in 400 ml of methanesulphonic acid. 80 g of chlorine were introduced into the solution at 10° to 20° C. (cooling with water). The reaction was allowed to continue until a sample, which was obtained by extracting the reaction mixture with hexane, showed no IR absorption at 1,610 $cm^{-1}$. The complete reaction solution was then extracted with hexane. 156 g (=80% of theory) of 2,5,5-trichloro-3,3-dimethylpentanoic acid-chloride of the boiling point range 92° to 95° C./0.12 mm Hg were obtained from the hexane phase by vacuum distillation, after the hexane had been expelled.

EXAMPLE 2

Preparation of the starting materials 75 g of vinyl chloride were introduced into a solution of 15 g of $AlCl_3$ in 1,000 ml of methylene chloride at −20° C., and 500 g of 1,3,3,3-tetrachloro-1,1-dimethyl-propane and a further 105 g of vinyl chloride were simultaneously metered into the reaction solution during the course of 180 minutes. The reaction mixture was thereafter allowed to react further for 180 minutes at −10° C., and 1,000 ml of water were then added to the solution. After the separation, the aqueous phase was extracted several times with methylene chloride, and the combined organic phases were dried with zeolite and fractionally distilled. 230 g of the starting material of the boiling point range 32° to 37° C. 0.1 mm Hg and 270 g of 1,1,5,5-tetrachloro-3,3-dimethyl-pent-1-ene (a compound of the formula (II)) of the boiling point range 72° to 76° C./0.15 mm Hg were obtained. This result corresponded to a conversion of 54% with a selectivity of 88%.

EXAMPLE 3

Further processing of the product obtained according to Example 1 to give caronaldehyde acid 100 ml of water are initially introduced into a stirred vessel and heated to 100° C. 63 g (0.25 mol) of 2,5,5-trichloro-3,3-dimethylpentanoic acid-chloride and a solution of 58 g of NaOH in 100 ml of water were then simultaneously added dropwise, the pH being monitored, at such a rate that a pH value in the range of 9 to 10 was maintained. The reaction had ended after 30 minutes. The reaction solution was cooled to 20° C., adjusted to pH 2 with hydrochloric acid and extracted with dichloromethane. After the solvent had been expelled, 36 g of crude acid were obtained, and, after distillation in vacuo, 29.6 g (=83.4%) of pure trans-3-formyl-2,2-dimethyl-cyclopropane-1-carboxylic acid, boiling point 125° to 130° C./0.5 mm Hg, were obtained.

$^1H$-NMR: δ=1.3 (s, 3H), 1.35 (s, 3H), 2.46 (m, 2H) 9.55 (d, resolved, 1H) 10.95 (s, 1H) ppm.

EXAMPLE 4

A mixture of 160 g of $Br_2$ and 71 g of $Cl_2$ (BrCl), and simultaneously 208 g of 1,1-dichloro-3-methyl-butene, were added dropwise to 770 g of methanesulphonic acid, while stirring. The reaction mixture was kept at 20° C. by cooling with ice. After a reaction time of 5 hours, 400 ml of ethanol were added dropwise and the reaction mixture was left for a further 5 hours at 60° C. The product mixture was then introduced onto 1 kg of ice and was extracted several times with toluene. 159 g of ethyl 2-bromo-3-methyl-butanoate, boiling point 80°-81° C./16 mm Hg, were obtained by fractional distillation of the organic phase.

EXAMPLE 5

600 g of 1,1,5-trichloro-3,3-dimethyl-pentene were added dropwise to 1,800 g of methanesulphonic acid, and 250 g of chlorine were introduced into the methanesulphonic acid, the mixture being stirred and the reaction temperature being 15° to 20° C. After 6 hours, 1,000 ml of ethanol were added and the mixture was warmed to 80° C. for a further 8 hours. After the working-up as in Example 4, 490 g of ethyl 2,5-dichloro-3,3-dimethyl-pentanoic acid, boiling point 80° to 85° C./0.3 mm Hg, were obtained.

EXAMPLE 6

336 g of 1,1,5-trichloro-3,3-dimethyl-pentene were reacted, in 1,000 g of methanesulphonic acid, with 210 g of chlorine, as described in Example 5. The end of the reaction was determined by IR spectroscopy. The reaction mixture was thereafter extracted several times with n-hexane. 252 g of 2,5-dichloro-3,3-dimethyl-pentanoic acid-chloride, boiling point of 65°-68° C./0.2 mm Hg, were obtained by fractional distillation of the hexane phase.

EXAMPLE 7

1,1-dichloro-3,3-dimethyl-5-fluoro-pentene was obtained by heating 500 g of 1,1,5-trichloro-3,3-dimethyl-pentene with 200 g of KF in 1,500 g of sulpholane for 8 hours, followed by fractional distillation; the compound boiled at 60° to 63° C./12 mm Hg.

58 g of 1,1-dichloro-3,3-dimethyl-5-fluoro-pentene was reacted with 39 g of chlorine in 193 g of methanesulphonic acid, as described in the examples above. After the reaction mixture had been extracted several times with n-hexane and the extracts had been fractionally distilled, 49 g of 2-chloro-5-fluoro-3,3-dimethyl-pentanoic acid-chloride, boiling point 75°-78° C./13 mm Hg, were obtained.

EXAMPLE 8

153 g of 1,1-dichloro-3,3-dimethyl-butene were reacted, in 500 g of methanesulphonic acid, with 151 g of BrCl, as indicated in Example 4. After the reaction had ended, the mixture was extracted with hexane and the extracts were worked up by distillation. 120 g of 2-bromo-3,3-dimethyl-butanoic acid-chloride of the boiling point range 60° to 65° C./15 mm Hg were obtained.

EXAMPLE 9

3,3-Dimethyl-1,1,5-trichloro-1-pentene 20 g of aluminum chloride were dissolved in 2,300 g of 1,1-dichloro-ethene, while stirring and cooling to −10° C. 1,286 g. of 1,3-dichloro-3-methyl-butane were then added dropwise to the solution during the course of 3 hours, and, at intervals of 15 minutes, a further 3 g of aluminum chloride in each case was simultaneously metered into the mixture, a reaction temperature of between 0° C. and +5° C. being maintained by cooling. After the reaction had eneded, 60 ml of acetic acid were added dropwise to the reaction mixture. The product mixture was thereafter filtered over Na₂SO₄ and was then metered into a distillation apparatus, the bottom temperature being kept at 120° C. and a pressure of 1 mbar being maintained; the distillate was cooled and condensed by a dry ice/acetone mixture. The crude distillate was then fractionated in vacuo in a Vigreux column.

1,650 g (=90% of theory) of 3,3-dimethyl-1,1,5-trichloro-1-pentene were obtained.

Boiling point 59° to 63° C./0.1 mm Hg.

EXAMPLE 10

23.6 g of 1,1,5,5-tetrachloro-3,3-dimethyl-pentene were added to 200 ml of concentrated sulphuric acid at 0° C., and 15 g of chlorine were then introduced into the mixture at 10° to 20° C., the reaction mixture being stirred intensively. After a sample of the reaction mixture, after extraction with hexane, had shown by means of IR spectroscopy that the absorption at 1,600 cm⁻¹ had vanished, excess chlorine was stripped off in vacuo. 400 ml of water were then added while stirring and cooling well, the temperature increasing to 70° C. After the mixture had been extracted with methylene chloride and the solvent had been distilled off, 22 g of crude 1,5,5-trichloro-3,3-dimethyl-pentanoic acid were obtained. This was converted into the acid-chloride by warming with 24 g of thionyl chloride, and the acid-chloride was isolated in pure form by fractional distillation. 17.2 g of 1,5,5-trichloro-3,3-dimethyl-pentanoic acid-chloride, boiling point 95° to 98° C./0.3 mm Hg, were obtained.

It will be appreciated that the instant specification and examples are set forth by way of illustration and not limitation, and that various modifications and changes may be made without departing from the spirit and scope of the present invention.

I claim:

1. A process for the production of a substituted α-halogenopropionic acid or derivative thereof of the formula

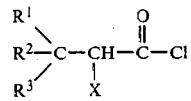

wherein
R¹ is a hydrogen or halogen atom, or an alkyl, halogen-substituted alkyl or aryl group,
R² and R³ each independently is a hydrogen or halogen atom or a methyl or ethyl group, and
X is a chlorine or bromine atom,
comprising reacting a substituted vinylidene chloride of the formula

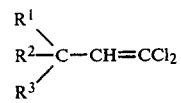

with chlorine or bromine chloride in the presence of a compound of the formula

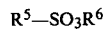

wherein
R⁵ is an optionally halogen-substituted C₁ to C₁₈ alkyl group, an optionally alkyl-substituted aryl group, a C₁ to C₈ alkoxy group, a chlorine or fluorine atom or a hydroxyl group, and
R⁶ is a hydrogen atom or a methyl or ethyl group.

2. A process according to claim 1, wherein
X is a chlorine atom,
$R^1$ is a hydrogen atom or a $C_1$ to $C_{13}$ alkyl group which is optionally substituted by fluorine, chlorine or bromine, and
$R^2$ and $R^3$ each independently is a hydrogen or halogen atom or a methyl or ethyl group.

3. A process according to claim 2, wherein
$R^1$ is a hydrogen atom, a $C_1$ to $C_{13}$ alkyl group or a $C_1$ to $C_4$ alkyl group which is substituted by 1 or 2 chlorine or fluorine atoms, and
$R^2$ and $R^3$ each independently is a hydrogen or chlorine atom or a methyl group.

4. A process according to claim 1, wherein the reaction is carried out at a temperature between about $-20°$ C. and $100°$ C.

5. A process according to claim 1, wherein about 1 mol of chlorine or 2 mols of bromine chloride are used per mol of vinylidene chloride.

6. A process according to claim 5, including the further step of reacting the acid choride with water thereby to form

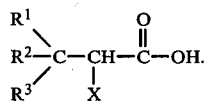

7. A process according to claim 5, including the further step of reacting the acid chloride with an alcohol of the formula

$R^4OH$ wherein $R^4$ is a $C_1$ to $C_8$ alkyl group, thereby to form

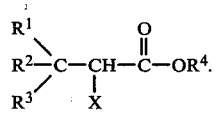

8. A compound selected from the group consisting of 2,5-dichloro-3,3-dimethyl-pentanoic acid, 2,5,5-trichloro-3,3-dimethyl-pentanoic acid, 2-bromo-5,5-dichloro-3,3-dimethyl-pentanoic acid and 2-chloro-5-fluoro-3,3-dimethyl-pentanoic acid.

9. 1,1,5,5-tetrachloro-3,3-dimethyl-pentene-1 of the formula

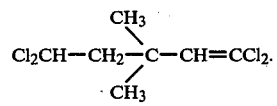

10. A process for the production of the compound according to claim 9, comprising reacting 1,3,3,3-tetrachloro-1,1-dimethyl-propane with vinyl chloride in the presence of a Lewis acid.

11. A process according to claim 10, wherein the reaction is carried out at a temperature between about $-20°$ C. and $+30°$ C.

12. A process according to claim 10, wherein the Lewis acid is $AlCl_3$, $FeCl_3$, $ZnCl_2$ or $TiCl_4$.

13. A process for the production of a substituted α-halogenopropionic acid or ester thereof of the formula

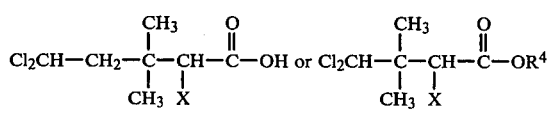

wherein
$R^4$ is a $C_1$ to $C_8$ alkyl group, and
X is a chlorine or bromine atom,
comprising reacting 1,3,3,3-tetrachloro-1,1-dimethyl-propane with vinyl chloride in the presence of a Lewis acid to form 1,1,5,5-tetrachloro-3,3-dimethyl-pentene-1, reacting the vinylidene chloride with chlorine or bromine chloride in the presence of a compound of the formula

$R^5-SO_3R^6$ wherein
$R^5$ is an optionally halogen-substituted $C_1$ to $C_{18}$ alkyl group, an optionally alkyl-substituted aryl group, a $C_1$ to $C_8$ alkoxy group, a chlorine or fluorine atom or a hydroxyl group, and
$R^6$ is a hydrogen atom or a methyl or ethyl group, to form the acid chloride of the formula

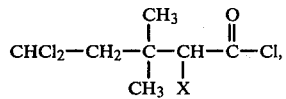

and reacting the acid choride with water or an alcohol of the formula $R^4OH$.

14. A substituted α-halogenopropionic acid of the formula

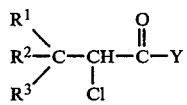

wherein
$R^1$ is a $C_1$ to $C_4$ alkyl group,
$R^2$ is a $C_1$ to $C_4$ alkyl group,
$R^3$ is a halogen-substituted $C_1$ to $C_4$ alkyl group, and
Y is a chlorine atom or a hydroxyl group.

* * * * *

UNITED STATES PATENT AND TRADEMARK OFFICE
CERTIFICATE OF CORRECTION

PATENT NO. : 4,440,947
DATED : April 3, 1984
INVENTOR(S) : Dieter Arlt

It is certified that error appears in the above-identified patent and that said Letters Patent is hereby corrected as shown below:

On the title page:
Under "U.S. Patent Documents", line 7     Delete "Scheidmeiu" and substitute --Scheidmeir--

Col. 4, lines 58, 65     Delete "$OCl_4 \longrightarrow OCl_3$" and substitute --$CCl_4 \longrightarrow CCl_3$--

Col. 7, line 63     Delete "eneded" and substitute --ended--

Signed and Sealed this

Thirteenth Day of November 1984

[SEAL]

Attest:

GERALD J. MOSSINGHOFF

Attesting Officer     Commissioner of Patents and Trademarks